(12) United States Patent
Smith

(10) Patent No.: US 10,245,295 B1
(45) Date of Patent: Apr. 2, 2019

(54) NEUROLOGICAL ESSENTIAL OIL COMPOSITION AND METHODS

(71) Applicant: Laura Harris Smith, Old Hickory, TN (US)

(72) Inventor: Laura Harris Smith, Old Hickory, TN (US)

(73) Assignee: Laura Harris Smith

( * ) Notice: Subject to any disclaimer, the term of this patent is extended or adjusted under 35 U.S.C. 154(b) by 0 days.

(21) Appl. No.: 15/711,125

(22) Filed: Sep. 21, 2017

(51) Int. Cl.
| | |
|---|---|
| *A61K 36/00* | (2006.01) |
| *A61K 36/899* | (2006.01) |
| *A61K 36/67* | (2006.01) |
| *A61K 36/9068* | (2006.01) |
| *A61K 36/53* | (2006.01) |
| *A61K 36/14* | (2006.01) |
| *A61K 36/328* | (2006.01) |

(52) U.S. Cl.
CPC ............ *A61K 36/899* (2013.01); *A61K 36/14* (2013.01); *A61K 36/328* (2013.01); *A61K 36/53* (2013.01); *A61K 36/67* (2013.01); *A61K 36/9068* (2013.01)

(58) Field of Classification Search
None
See application file for complete search history.

(56) References Cited

U.S. PATENT DOCUMENTS

| 2003/0014096 A1* | 1/2003 | Burkhart | ................... A61F 7/02 607/109 |
| 2011/0274643 A1* | 11/2011 | Yontz | ....................... A61K 8/25 424/76.1 |

\* cited by examiner

*Primary Examiner* — Qiuwen Mi

(57) ABSTRACT

This is a neurological essential oil composition employing oils containing sesquiterpene compounds that cross the blood-brain barrier, such as Vetiver, Black Pepper, Ginger, Ylang Ylang, Sandalwood, Patchouli, Cedarwood, Myrrh, Frankincense, or Lavender, offering calming relief from seizures, migraine, anxiety, tremor, PTSD, and other neurological ailments, minus side-effects often experienced with conventional neurotherapeutics. A case study using FDA guidelines was conducted on the composition by the inventor/nutritionist treating these disorders and more with success, including her own seizure disorder. For neurological stimulation to improve cognitive function, the composition recruits oils such as Coffee, Vanilla, Cinnamon Bark, Clove, Dalmatian Sage, Rosemary, Blood Orange, Lemon, Grapefruit, Peppermint, Lime, Clementine, Spearmint or Coconut. The invention is applied directly to the skin and is also present in other topical administrations such as shampoo, conditioner, lotion, face wash, body wash, bath salts, and in aromatherapy administrations such as candles, nasal inhalers and sprays.

3 Claims, No Drawings

NEUROLOGICAL ESSENTIAL OIL COMPOSITION AND METHODS

FIELD OF THE INVENTION

The invention generally relates to the field of essential oil compositions for human therapeutic use, in particular, essential oil compositions and methods for neurological therapeutic support, gaining access to the central nervous system by crossing the blood brain barrier and bringing calm during seizures, migraines, panic attacks, insomnia, tremors, PTSD, etc., and providing stimulation when treating depression, dementia, impaired communication, cognitive malfunctions, and more. This happens primarily through the topical use of the oil blend itself but also by its inclusion into topical body applications including, but not limited to lotion, shampoo, conditioner, body wash, face wash, and bath salts, and secondarily through aromatherapy, which gains access to the limbic brain through the nasal passages once the oils are inserted into scent-based carriers including but not limited to nasal inhalers, candles and sprays.

BACKGROUND OF THE INVENTION

In the 2014 Society for Neuroscience article entitled "The Blood Brain Barrier," it says, "The brain is the only organ known to have its own security system, a blood vessel network that allows the entry of essential nutrients while blocking other substances. Unfortunately, this barrier is so effective at protecting against the passage of foreign substances that it often prevents life-saving drugs from being able to repair the injured or diseased brain."[1]

[1] Mary Bates, "The Blood-Brain Barrier," Society for Neuroscience, Jul. 2, 2014, brainfacts.org/brain-basicsineuroanatomy/articles/2014/blood-brain-barrier, [Live link removed per 37 CFR 1.57(e)].

NeuroRX, the journal of the American Society for Experimental NeuroTherapeutics, agrees, stating in their 2005 article about the blood-brain barrier, "The blood-brain barrier (BBB) is formed by the brain capillary endothelium and excludes from the brain ~100% of large-molecule neurotherapeutics and more than 98% of all small-molecule drugs." Their article, "The Blood-Brain Barrier: Bottleneck in Brain Drug Development"[2] was published by The National Center for Biotechnology Information (NCBI), which is part of the trusted United States National Library of Medicine (NLM), a branch of the National Institutes of Health. This means that an estimated 98 percent of all drug treatments for brain disorders are unable to even infiltrate the blood-brain barrier, and 100 percent of today's traditional treatments are unable to aid the brain at all if their molecular compound is too large. Imagine the implications: millions upon millions of suffering neurological patients who take daily medicine but can find no consistent relief from their neurological diseases. And for many who do, the relief comes at the high price of countless side effects, which often include more neurological malfunctions and manifestations.

[2] William M. Pardridge, "The Blood-Brain Barrier: Bottleneck in Brain Drug Development," NeuroRx*: The Journal of the American Society for Experimental NeuroTherapeutics 2, no. 1 (2005), ncbi.nlm.nih.gov/pubmed/15717053, [Live link removed per 37 CFR 1.57(e)], The article goes on to say: "Despite the importance of the BBB to the neurotherapeutics mission, the BBB receives insufficient attention in either academic neuroscience or industry programs. The combination of so little effort in developing solutions to the BBB problem, and the minimal BBB transport of the majority of all potential CNS (Central Nervous System) drugs, leads predictably to the present situation in neurotherapeutics, which is that there are few effective treatments for the majority of CNS disorders."

Essential Oils Cross the Blood Brain Barrier

New information is slowly nudging researchers to invent new ways to open this barrier and "trick" it into allowing medicines to enter. Far from new, sesquiterpene essential oils are one of these creative "tricks," are all natural, and have been around since the beginning of time as have all other categories of essential oils.

According to WebMD and Healthwise Incorporated, "Essential oils are taken from a plant's flowers, leaves, stalks, bark, rind, or roots. The oils are mixed with another substance (such as oil, alcohol, or lotion) and then put on the skin, sprayed in the air, or inhaled. You can also massage the oils into the skin or pour them into bath water. They also state that Aromatherapy originated in Europe in the early 1900s."[3]

[3] "Aromatherapy (Essential Oil Therapy) Topic Overview," Healthwise, Incorporated, webmd.com/balance/stress-management/tc/aromatherapy-essential-oils-therapy-topic-overview#1. [Live link removed per 37 CFR 1.57 (e).]

David Stewart, Ph.D., R. A is a Registered Aromatherapist and the author of Healing Oils of the Bible (Care Pub., 2003). One of his many articles on the healing properties of oil, "The Blood-Brain Barrier" contains a remarkable quote based on his studies. He says: "The American Medical Association (AMA) has said that if they could find an agent that would pass the blood-brain barrier, they would be able to find cures for ailments such as Lou Gehrig's disease, multiple sclerosis, Alzheimer's disease, and Parkinson's disease. Such agents already exist and have been available since Biblical times. The agents, of course, are essential oils-particularly those containing the brain oxygenating molecules of sesquiterpenes."[4]

[4] Dr. David Stewart, "The Blood Brain Barrier," (Raindrop Messenger Archive) Ph.D., R. A, raindroptraining com/messenger/vinl.html#one, January, 2003. [Live link removed per 37 CFR 1.57(e)].

Dr. Stewart adds, "Doctors don't know for sure, but it seems that in order to cross the blood-brain barrier, only molecules less than 800-1000 atomic mass units (AMU) in molecular weight can get through. Lipid solubility seems to be another factor that facilitates passing through the BBB. Water soluble molecules don't usually penetrate into brain tissue, even when very small. The molecules of essential oils are all not only small but lipid soluble as well. Sesquiterpene molecules deliver oxygen molecules to cells, like hemoglobin does in the blood."

This is the importance behind the inclusion of sesquiterpene oils in this invention. They provide a vehicle for the blend to cross the blood brain barrier and reach the physiological sectors that are home to disorders like epilepsy, migraine, depression, insomnia, memory loss and more. The other classifications of oils selected in claims 3 and 4 (monoterpenes, ketones, eugenols, phenols, oxides, etc.) are also helpful to the brain, more so for stimulating cognitive abilities and lifting mood, and the good news is that many of them do also contain measures of sesquiterpene compounds to assist the blend in reaching its urgent destination to the brain of the patient in need. (See such success stories under "Samples of Treatment.")

Aromatherapy

Earlier, NeuroRX's findings were cited concerning how the brain entirely excludes (won't accept) "100% of large-molecule neurotherapeutics and more than 98% of all small-molecule drugs." Only the tiniest of biologic molecules can pass through the brain's security system otherwise known as the blood-brain barrier. In the words of Dr. Stewart, "When it comes to essential oils, small molecules (less than 500

AMU) are what they are made of. That is why they are aromatic. The only way for something to be aromatic is for the molecules to be so small that they readily leap into the air so they can enter our noses and be detected as odor and smell."

Like Dr. Stewart, Brent Bauer, M.D., Director of the Complementary and Integrative Medicine program at the Mayo Clinic, has studied the effects of essential oils on numerous illnesses. In a 2014 Women's Health article, Dr. Bauer is quoted as saying of essential oils, "The plant-extracted, highly concentrated liquids have historically been selling points in beauty and cleaning products—and now research proves that when inhaled properly, they're also good medicine."[5] He is also quoted directly on Mayo Clinic's website as saying, "Aromatherapy is thought to work by stimulating smell receptors in the nose, which then send messages through the nervous system to the limbic system—the part of the brain that controls emotions."[6] Dr. Bauer also says, "The highly concentrated oils may be inhaled directly or indirectly or applied to the skin through massage, lotions or bath salts," adding, "Some studies have shown that aromatherapy might have health benefits, including: relief from anxiety and depression; improved quality of Society for Neuroscience, particularly for people with chronic health conditions; improved sleep."

[5] Tori Rodriguez, "6 Scents That Have the Power to Heal" Women's Health, May 23, 2014.
[6] Brent A. Bauer, M.D., What are the Benefits of Aromatherapy?" Mayo Clinic, Feb. 5, 2015, mayoclinic.org/healthy-lifestyle/consumer-healthiexpert-answersiaromatherapy/faq-20058566. [Live link removed per 37 CFR 1.57(e)].

Your sense of smell is the only one of your five senses that is directly tied to the limbic area of your brain, which is described by many experts as the emotional control center of the brain. Both sesquiterpene and monoterpene class oils (plus many other classes) can access the limbic brain through inhalation. So, even though essential oils are very effective when absorbed topically or taken internally, when inhaled they go directly to your brain. All of your other senses—taste, hearing, seeing and touch—journey first to the thalamus before reaching designated areas of the brain.

This limbic system-scent relationship is good news to those with stress or anxiety disorders because they can experience expedient change and oftentimes, relief, by just smelling essential oil or by diffusing it in the air. Each tiny oil molecule that you inhale travels through your nasal passages to a receptor neuron that carries it at the speed of smell to the limbic brain, and onto whatever needs relief in its jurisdiction. In other words, these healing messengers in your nasal cavities have direct access to your brain. But no matter if you smell, rub or ingest your sesquiterpenes, research shows they can also permeate the skin, travel nerve pathways, cross the blood-brain barrier and impart balance and health, reportedly even erasing or deprogram miswritten codes in the DNA even at the cellular level. This is consistent with "DNA resetting" research being done by popular immunologists with the help of John Hopkins University:

In an article entitled, "Human Electrical Frequencies and Fields," published by Quantum Health Consulting, Gary Young says, "Bruce Tainio, of Tainio Technology and head of the Department of Agriculture at Eastern Washington University, has developed a Calibrated Frequency Monitor (CFM) that has been used to measure the frequencies of essential oils and their effect on human frequencies when applied to the body. One popular essential oils laboratory uses a CFM, and another is located at Johns Hopkins University where it is used to study frequency in relationship to disease."[7]

[7] D. Gary Young, "Human Electrical Frequencies and Fields," Quantum Health Consulting, 1996-99, quantumhealthconsulting.com/human-electrical-frequencies-and-fields/. [Live link removed per 37 CFR 1.57(e)].

He adds, "it seems some essential oils have a reset function. It can tell the cell what the right DNA code should be," citing Immunologist Mahmoud Suhail, who says, "Cancer starts when the DNA code within the cell's nucleus becomes corrupted."

Frequencies, Health and Essential Oils

Young goes on to cite a study that adds something significant to the discussion on oils for this invention: "Frequency is defined as a measurable rate of electrical energy flow that is constant between any two points. Everything has an electrical frequency, and what an incredible discovery it was for me to learn that essential oils contain frequencies that are several times greater than the frequencies of herbs and foods." Robert O. Becker, M.D., the author of the book, *The Body Electric* (William Morrow Paperbacks; 1st ed., July 1998), validates the electrical frequency of the human body. In clinical trials, Young measured the various frequencies of various objects and their effects on the human body. He says, "Measuring in hertz, we found that processed/canned food had a zero Hz frequency, fresh produce had up to 15 Hz, dry herbs from 12-22 Hz, and fresh herbs from 20-27 Hz. Essential oils started at 52 Hz and went as high as 320 Hz, which is the frequency of rose oil. A healthy body, from head to foot, typically has a frequency ranging from 62 to 78 Hz, while disease begins at 58 Hz. Clinical research shows that essential oils have the highest frequency of any natural substance known to man, creating an environment in which disease, bacteria, virus, fungus, etc., cannot live." In one clinical trial, a man with a body frequency of 66 Hz fell to 58 Hz after holding a cup of coffee for 3 seconds, and his frequency did not return to normal for three days. A different man drank the coffee and his bodily frequency dropped to 52 Hz from 66 Hz. He then inhaled a proprietary blend of essential oil and his frequency jumped back up to 66 Hz in only 21 seconds.

Essential Oils with Prayer

The reason this is significant to this invention is because Young also discovered that the frequency of the oils themselves changed with words and prayer. He says, "We respond to the thoughts and prayers of others, whether we are aware of it or not, and so do essential oils. In some of Bruce Tainio's work, essential oils were measured before and after being bombarded with negative thoughts. Their frequencies went down by 12 MHz. When positive thoughts were aimed at the oils, their frequencies went up by 10 MHz. When the oils were prayed over, their resonant frequencies went up by 15 MHz. Oils amplify intent. And intent will move molecules of oil to where they can best serve to heal. This is why prayer and anointing with essential oils work so well when combined together."[8]

[8] Ralf Kollinger, "Aromatherapy Essential Oil Frequency," quantumhealthconsulting.com/human-electrical-frequencies-and-fields/[Live link removed per 37 CFR 1.57(e)].

These studies provide the science behind why this composition is considered to be, in some circles, a therapeutic anointing oil. And perhaps this gives new insight into the New Testament book of James, chapter 5, verses 14-15:

"Is anyone among you sick? Let them call the elders of the church to pray over them and anoint them with oil in the name of the Lord; and the prayer offered in faith will make the sick person well; the Lord will raise them up."[9]

[9] Holy Bible, New International Version®, NIV® Copyright© 1973, 1978, 1984, 2011 by Biblica, Inc.® All rights reserved worldwide.

This is also why prayer is considered to be part of the oil's unique "recipe" and why each batch receives prayer by ordained clergy.

PRIOR ART

Evidence has already been cited herein concerning the reported inability of many modern neurotherapeutic drugs to pass through the blood-brain barrier and treat the brain, and how researchers are discovering that certain essential oils can (sesquiterpenes). But as for searching for prior art within patent searches, this exact present composition has not been found. The closest thing discovered was U.S. Pat. No. 6,579,543B1, which is an essential oil composition for animals to be used topically after injuries and not for human treatment and that may or may not include the oils in this new invention seeking protection. Their approved patent claims that in addition to multiple vitamins and herbs, the composition contains "one or more essential oils" and then lists 74 oils from which they can choose, some of which are in this composition in consideration, including lavender, sandalwood, cedarwood and patchouli. However, it does not include the potently strong sesquiterpene oils of vetiver, myrrh and frankincense (which is only part-sesquiterpene), nor does it contain the mood-lifting essential oils of coffee, vanilla, dalmatian sage, clementine, or blood orange as does this new composition. And again, U.S. Pat. No. 6,579,543B1 is a patent for the treatment of animals and not for humans. Their patent reads, " . . . relief of the signs and symptoms of pain and/or inflammation in a human subject may be less than desired because of the lack of an effective delivery system for reaching the tissue from which the pain and/or inflammation are originating." This new invention has proven successes on human subjects (see such successes under "Samples of Treatment").

With more than 600 medically documented neurological conditions affecting hundreds of millions of people all over the world, this invention's essential oil composition is a brain-nourishing proprietary oil blend created to offer neurological relief for those who suffer with them, made entirely of the aforementioned therapeutic grade essential oils. Although there is not currently a way to test this invention on people from all 600 neuro-graphics, there is ample research that shows that each of these composition's essential oils—especially the sesquiterpenoids—have individually been internationally successful in helping naturally regulate the brains of people who are subject to seizures, anxiety, Parkinson, Alzheimer's, PTSD, Lou Gehrig's, Multiple Sclerosis, Muscular Dystrophy, concussion, stroke, migraines. restless leg syndrome, sensory issues, shingles, sleep apnea, palsies, tremors, pituitary tumors, learning disorders, and many, many more. Some of those studies' information is cited below under the descriptions of each of the sesquiterpene oils in this composition.

After researching patent archives for prior art, it appears feasible that this composition is the first oil blend to bring all of these sesquiterpenoids together in this fashion and for these exact human neurological challenges. As for the oils mentioned in claims 3 and 4, no prior art could be found which comprises combinations of those oils for their precise neurological purposes stated in its claim (to stimulate the human brain to improve memory, increase concentration, lift mood and to serve as an anti-depressant). Coffee essential oil is also fairly new to the retail scene of essential oils and so its inclusion into another neurological composition of this nature was unable to be located.

Here are the individual benefits from each of this invention's sesquiterpene essential oils listed as 2-18% oil from the grasses of *Vetiveria zizanioides* (Vetiver oil), 2-12% oil from the dried berries of *Piper nigrum* (Black Pepper oil), 3-15% oil from the roots of *Zingiber officinale* (Ginger oil), 7-23% oil from the flowers of *Cananga odorata* (Ylang Ylang oil), 7-23% oil from the wood of *Santalum spicatum* trees (Sandalwood oil), 11-27% oil from the leaves of *Pogostemon cablin*, (Patchouli oil), 5-31% oil from the wood of *Juniperus virginiana* (Cedarwood oil), and 7-23% oil from the resin of *Commiphora myrrha* (Myrrh oil), 5-25% oil from the flowers of *Lavandula officinalis* (Lavender oil), or 10-26% oil from the resin of *Boswellia carterii* trees (Frankincense oil), followed by a very brief overview of the benefits of the additional oils including 6-28% oil from the peel of *Citrus sinensis* (Blood Orange oil), 2-26% oil from the leaves of *Salvia officinalis* (Dalmatian Sage oil), 4-19% oil from the leaves from *Rosmarinus officinalis* (Rosemary oil), 4-24% oil from the peel of *Citrus limonum* (Lemon oil), 5-21% oil from the peel of *Citrus paradisi* (Grapefruit oil), 3-13% oil from the leaves of *Mentha piperita* (Peppermint oil), 4-18% oil from the peel of *Citrus latifolia* Tanaka (Lime oil), 6-23% oil from the peel of *Citrus nobilis* (Clementine oil), or 7-27% oil from the leaves and stems of *Mentha spicata* (Spearmint oil), 4-16% oil from the seeds of *Coffea arabica* (Coffee oil), 4-22% oil from the fruit of *Vanilla planifolia* (Vanilla oil), 5-15% oil from the bark of *Cinamomum zeylanicum* (Cinnamon Bark oil), 3-13% oil from the buds of *Syzygium aromaticum* (Clove oil), and 2-12% oil from the kernels of *Cocos nucifera* (Coconut oil):

Vetiver (*Vetiveria Zanioides*) has an earthy fragrance similar to patchouli with a hint of lemon. Vetiver oil is psychologically calming and stabilizing. Vetiver may be useful in helping cope with stress and find relief from emotional traumas and stress syndromes.

*Piper Nigrum* (Black Pepper) oil is useful for those with anxiety or nervous disorders. For those reasons, it also is very helpful to those trying to stop smoking. One study, published in Drug and Alcohol Dependence in 1994, discovered that smoking withdrawal symptoms and cigarette cravings were greatly reduced when using black pepper oil. Also, the negative effects of the anxiety were totally alleviated with its use.[10]

[10] Behm, F. M., Rose, J. E., "Inhalation of vapor from black pepper extract reduces smoking withdrawal symptoms," National Center for Biotechnology Information, February 1994, https://www.ncbi.nlm.nih.gov/pubmed/8033760 [Live link removed per 37 CFR 1.57(e).]

*Zingiber Officinale* (Ginger) has been used historically in the treatment of dementia. Now studies show that it improves many more cognitive functions besides just the memory, including attention, reaction time and general mood. Acetylcholine, a neurotransmitter that plays a part in learning and memory, is increased in the brain by bioactive compounds found in ginger and specifically, ginger oil. Experts say that the best Alzheimer's drugs on the market utilize the same mechanisms.

Ylang Ylang (*Cananga Odorata*) may be extremely effective in giving a sense of relaxation and in balancing the central nervous system. It affects the glandular system, stimulates adrenal glands, while simultaneously being used for pain and insomnia. It has been known to have good results for lowering blood pressure, alleviating PMS, and easing the symptoms of depression. Ylang Ylang is said to quiet the emotions of fear, anxiety, anger, and worry.

Sandalwood (*Santalum Spicatum*) has relaxing, meditative prayer properties and is historically used in churches and temples. Sandalwood has been studied in Europe for its abilities to oxygenate a part of the brain known as the pineal gland, which produces melatonin, also known as the drowsy hormone. So, it is effective for quieting the brain and for helping achieve sleep in larger doses. Sandalwood is also reported to assist in eliminating negative programming from the body's cells.

Patchouli (*Pogostemon Cablin*) has been reported to be a mild sedative and very effective in decreasing the intensity of epileptic attacks. It can bring relief to tension stress, eases anxieties and promotes an overall sense of well being. Patchouli can be an effective stress buster, providing relaxation to the tired and stressed mind and body. Patchouli greatly benefits the nervous and glandular systems, and is known to be an anti-depressant, anti-inflammatory and antiseptic.

Cedarwood (*Juniperus Virginiana*) has been recognized historically for its quieting, purifying properties. It can alleviate stress with its warming and calming actions on the emotions. It is said to calm the nerves, and benefits many other body functions such as to relax tense muscles. The oil with the highest percentage of sesquiterpenes, Cedarwood is reported to supply oxygen to tissues and erase DNA damage. It works by stimulating the pituitary gland and naturally increasing the melatonin in the brain. This is why Cedarwood oil is effective for getting a good night's sleep.

Myrrh (*Commiphora Myrrha*) is an oil mentioned throughout the Bible ("A bundle of myrrh is my well-beloved unto me." Song of Solomon 1:13). With its high levels of sesquiterpenes, its compounds can have direct effects on the hypothalamus, pituitary, and amygdala. It is reported to be emotionally strengthening and has been used since ancient times as an antiviral, anti-fungal, antiseptic, and anti-inflammatory.

Frankincense (*Boswellia Carterii*), although not a primary carrier of sesquiterpenoids, does contain more than 30 compounds from the sesquiterpene and diterpene fractions. For that reason, coupled with its proven successes in neurological support, it won a place in the sesquiterpenoid line-up. It is considered a sacred anointing oil and has been used in religious rituals for thousands of years, even given as a gift by the Wise Men to the Christ-child (" . . . presented unto him gifts; gold, and frankincense, and myrrh." Matthew 2:11). It was popular even during the ministry of Christ for its anointing and healing powers. Frankincense is now being administered therapeutically in European hospitals. It slows down and deepens the breath, can strengthen the immune systems and help in overcoming stress. The therapeutic properties of Frankincense oil are antiseptic, astringent, and sedative in nature.

Lavender (*Lavandula Officinalis*) is not a primary carrier of sesquiterpenoids but does contain enough of it to gain it a reputation as "the relaxing oil" and for that reason was included in the category of calming oils. Lavender is also considered to be the most versatile of all essential oils. Thus, It has been clinically tested for its relaxing benefits and has also been proven in scientific studies to show efficacy in the treatment of agitated behavior in patients with severe dementia. In a 2012 NCBI article entitled, "The Effects of Lavender Oil Inhalation on Emotional States, Autonomic Nervous System, and Brain Electrical Activity," their conclusion was: "The findings provided evidence the relaxing effect of inhaling lavender oil."[11][12] It can trigger the body's "rest and digest" response, inducing relaxation. Lavender is also reported to ease mental confusion and depression and to decrease anxiety, insomnia and headache pain (even migraine).

[11] C. Holmes, V. Hopkins, C. Hensford, V. MacLaughlin, D. Wilkinson, H. Rosenvinge, "Lavender Oil as a Treatment for Agitated Behaviour in Severe Dementia: a Placebo Controlled Study." National Center for Biotechnology Information 2002, http://www.ncbi.nlm.nih.gov/pubmed/11994882 [Live link removed per 37 CFR 1.57(e).]

[12] W. Sayorwan, V. Siripornpanich, T. Piriyapunyaporn, T. Hongratanaworakit, N. Kotchabhakdi, N. Ruan-grungsi, "The effects of lavender oil inhalation on emotional states, autonomic nervous system, and brain electrical activity," National Center for Biotechnology Information, April 2012, http://www.ncbi.nlm.nih.gov/pubmed/22612017 [Live link removed per 37 CFR 1.57(e).]

Other than those sesquiterpene-bearing oils that this invention relies so heavily upon, many of the other oils listed in claims 3 and 4 also contain smaller properties of sesquiterpenes, as well as monoterpenes or other classes of oils which, on their own have tremendous neurological benefits. They and their botanical origins are: *Coffea Arabica* (Coffee), *Vanilla Planifolia* (Vanilla), *Cinnamomum Zeylanicum* (Cinnamon Bark), *Syzygium Aromaticum* (Clove), *Salvia Officinalis* (Dalmatian Sage), *Rosmarinus officinalis* (Rosemary), *Citrus Sinensis* (Blood Orange), *Citrus limonum* (Lemon), *Citrus Paradisi* (Grapefruit), *Citrus Latifolia* Tanaka (Lime), *Citrus Nobilis* (Clementine), *Mentha Piperita* (Peppermint), *Mentha spicata* (Spearmint), and *Cocos Nucifera* (Coconut). They have been attributed with the following 12 neurological benefits:

increasing concentration
improving memory
lifting mood
eliminating exhaustion
enhancing communication
reducing cognitive malfunction
boosting memory performance in Alzheimer's patients
stimulating blood circulation
increasing oxygen flow to the brain
acting as an antidepressant
decreasing learning deficits
assisting in weight loss

SUMMARY

This essential oil composition is composed of selected plants from amongst twenty-four specific genera whose leaves, grass, wood, buds, bark, seeds, stems, roots, berries, peels, fruit and flowers are steam-distilled to produce sesquiterpene-class oils capable of crossing the blood-brain barrier, and monoterpene and other class oils which offer human therapeutic neurological relief when administered through topical or aroma-therapeutic methods. Essential oils are also all natural and free of the side-effects common to most neurotherapeutic drugs.

The oils available for use in this composition are *Vetiveria Zanioides* (Vetiver), *Piper Nigrum* (Black Pepper), *Zingiber Officinale* (Ginger), *Cananga Odorata* (Ylang Ylang), *Santalum Spicatum* (Sandalwood), *Pogostemon Cablin*, (Patchouli), *Juniperus Virginiana* (Cedarwood), *Commiphora Myrrha* (Myrrh), *Coffea Arabica* (Coffee), *Vanilla Planifolia* (Vanilla), *Cinnamomum Zeylanicum* (Cinnamon Bark), *Zingiber Officinale* (Ginger), *Syzygium Aromaticum* (Clove), *Salvia Officinalis* (Sage), *Rosmarinus officinalis* (Rosemary), *Piper Nigrum* (Black Pepper), *Citrus Sinensis* (Blood Orange), *Citrus limonum* (Lemon), *Citrus Paradisi* (Grapefruit), *Citrus Latifolia* Tanaka (Lime), *Citrus Nobilis* (Clementine), *Mentha Piperita* (Peppermint), *Mentha spicata* (Spearmint), and *Cocos Nucifera* (Coconut).

All 24 of the aforementioned essential oils are considered part of the invention and may be used to help achieve a desired neurological result.

All ingredients in this essential oil composition are present in the varied arrangements and methods of its administrations. Those administrations include topically applying the oil blend directly to the skin, but the oil blend is also incorporated into products including but not limited to shampoo, conditioner, body wash, face wash, and body lotion applied directly to the body's skin, scalp, hair or face for topical administration. The oil composition is also present in varied methods of aromatherapy arrangements and inhaled through the nasal passages into the limbic brain by use of products including but not limited to nasal inhalers, paraffin candles and pillow spray.

The main objective of the invention and its methods of arrangements for usage includes but is not limited to: stopping a seizure in progress or lessening seizure frequency altogether with regular use, stopping migraine pain when given at onset of migraine episode, remedying insomnia, promoting relaxation, elevating mood during depressive episodes, supporting focus for ADD and ADHD sufferers, lessening the discomforting inconvenience of muscle spasms and tremors of neurological origin, lessening and eliminating the effects of shingles, generating calm in the presence of stress-related disorders such as PTSD, anxiety, phobias and fears, and providing overall neurological relief from disorders of the central nervous system and its various manifestations. Successes in treatment can be read in the next section entitled, "Samples of Treatment."

Studies cited in the Background of the Invention show that 98%-100% of all small or large molecule neurotherapeutic pharmaceutical drugs never pass through the blood-brain barrier to bring actual aid the distressed brain, but that there are a class of essential oils that will cross the blood-brain barrier, namely, sesquiterpene oils. Many oils used for this composition each have a sesquiterpene compound majority, and those that are not primarily made of sesquiterpenoids are still in the terpene family and do contain smaller, yet significant, levels of sesquiterpenes to act as a vehicle to carry the composition to its urgent destination: the brain of the patient in need. This invention serves as a great improvement to the neurotherapeutic drugs that often never reach the brains that need them.

The inventor has a 40-year medical history of epileptic seizures, is a certified nutritional counselor, an ordained pastor, and has created the composition after extensive scientific research, becoming the first person to benefit from it neurologically.

Samples of Treatment

In the Fall of 2016, the inventor conducted a case study using FDA guidelines and their release forms for participants. Participants were given the following administration instructions for topical use of the oil blend:
Where: This oil is to be used topically on the skin, preferably applied to the brainstem region on the back of the head where the base of the skull meets the top of the neck just under the hairline, or on the temples, crown of head, pulse points (wrists) or a mixture of these areas. Some with tremors have generously applied the oil generously directly to the leg, hand or other area.
Who: This oil is safe for all ages, but not to be applied "neat" (without dilution) for ages 3 and under. See below for applications.
How much: Rollerball Bottle: The recommended rollerball application is one light swipe across the brainstem region, then dots on temples and on wrists. That's 1 swipe and 4 dots. For children, first swipe skin lightly with a carrier oil (i.e. olive, coconut, grapeseed, etc.) then apply oil. Dropper Bottle: Place 5-6 drops on brainstem region, or share with temples and wrists. For children, dilute 5-6 drops in 1 tsp. carrier oil then apply as directed. Remember, the oil blend is not cut with any carrier oils.
When: A second application is allowed within 20 minutes of the first for urgent relief (i.e. migraine, seizures, anxiety, etc.) In this case, you may want to use your extra application strategically on the region of discomfort itself (leg, hand, fingers, head, etc.).
Aromatherapy: You may also diffuse your oil by placing 5-6 drops in a diffuser. Remember, too: inhalation of the oil itself is a direct pathway to the limbic brain and can bring quick relief. Both methods are effective additions to your topical applications. Note: Consult your physician or medical professional before beginning any new treatment regimen. Test on a patch of skin and if necessary, dilute with a carrier oil to minimize irritation. Avoid eyes.
Here are some of the results from the first users of this composition during the case study, in their own words. The testimonials are from males and females, ages 5 to age 92:
"It worked!!!!! I woke up to my son having cluster seizures. I got up and ran to my purse and got the oil blend. I put a little fractionated coconut oil on his forehead and rolled some on his head . . . then on the bottoms of his feet and temples. Within a minute or two the seizures stopped and he fell back to sleep!" (Mother of 5-year old epileptic boy. Condition: epilepsy, cerebral palsy)
"I wouldn't have thought that an essential oil or combination would impact me this much but it helped a lot. I could tell a big difference. I slept through the night and I have felt better today. I'm telling you, it was a big blessing because I've had a couple of nights that have been very difficult and last night was fine. Thank you! It eased my suffering." (66-year old female. Condition: Global Transition Amnesia, stress, memory loss)
"Day 1 and I am already amazed. This oil is unreal. I cannot even tell you the last time I felt legitimately relaxed. I've been on 5 different anxiety meds in my lifetime and got off all of them because they just did not work for me. All the background noise and anxious thoughts just aren't there. It's almost shocking because I haven't felt so calm in so long. Praise God!" (24-year old female. Condition: anxiety, panic attacks, numbness, racing thoughts.)
"For the first time in many years, I slept through to my alarm last night! Major-life-change-induced stress apparently kept my brain hyperactive at night. I recommend for anyone struggling with Chronic Fatigue, M.T.H.F.R. and/or insomnia. #IGotSleep (55 year male. Condition: insomnia, Chronic Fatigue)
"It's been amazing for me. The effects are cumulative, FYI. The longer I use them the more consistent and obvious the calm is. [My wife] really noticed it the other day. I handle things with 100 times more ease it feels like. So unlike the lavender or [other oils] that works kind of the same each time and the effects last the half life, I think this heals or redirects pathways so that each time the effects are more obvious. I'm noticing ascetic values in things again, if that makes sense, which means my mind is getting away from the lizard brain. My brain feels like it's trying to find a new center, I think. I'm baffled that it's worked like it has. It has to be the amounts and combo because those oils individually have never worked like that." (33-year old male, veteran. Condition: PTSD)
"I've used [the oil] for migraine headaches, anxiety and stress. At the onset of a migraine I will experience the appearance of sensory auras, spots or flickering light. I even will lose some vision, usually in my left eye. After applying [the oil] to the inside of both wrists as well as my temples within 5 minutes the headache was gone or I avoided a full blown migraine. All symptoms were gone! When using the oil blend for anxiety or stress; after applying it to the inside of both wrists as well as my temples within 10-15 minutes, I felt calm and relaxed. I would definitely recommend the oil to others and will continue to keep it readily available. Thanks, Laura, for allowing God to inspire you to create this wonderful blend of oils. My daughter has had migraines several times and I've shared it with her. She loves it!" (53-year old female. Condition: migraines, anxiety and stress)

"After ONE NIGHT of [my son's] use of the oil blend he has already noticed some very positive changes. He slept the whole night for the first time in a long time.

We are looking forward to even more positive feedback as the days go by. Thank you for such a blessed product, Laura!" (Mother of 20+ year old son. Condition: insomnia)

"I suffered from anxiety attacks after a long drawn out traumatizing divorce, doctors have tried several different types of anti-depressants and anxiety drugs . . . and through this product I was . . . set free. I've gained my confidence back and have been able to drive. Before I couldn't drive a few blocks away from home before an attack would occur. If you only knew the paralyzing moments I've had at the worst times, while picking up a grandchild from [school], praying not to have an attack and on my way back . . . . I have to pull off in a parking lot to calm down. This is before I heard about your product. If I could have gotten this to my son sooner he would have been able to finish boot camp. He quit last week due to anxiety attacks. When he got home he couldn't sleep the first night and called me early in the morning. I asked him to come to my job and I gave him what I had left of the oil and anointed him with it. No more sleepless nights or anxiety for him. I plan on never running out again or ever running low for any of us. I share the testimonial with everyone . . . since experiencing this miracle." (63-year old female. Condition: anxiety, fear, panic attacks)

"Those who personally know me know the daily (and I mean daily) painful struggles I encounter. Nonetheless, I was part of this oil blend case study to see how well the benefits were for someone suffering from a SCI (spinal cord injury). Amazingly enough, I saw benefits that brought joy to my heart and relief to my physical body. My muscle spasms lessened greatly and I was able to sleep at night. This blend is undiluted and potent. Over my 5½ years I've used many things to help find relief with spasms. Nothing has helped. This is the only legal retail product that I've found (including prescription drugs) that gives me the results I need to live a somewhat normal life." (40-year old female. Condition: spinal cord injury with leg spasms)

"My mother says it has helped relieve her tremor. Not totally ameliorated it but makes it less intolerable. Hurrah for that. I've found it lessens my [own] tremor when doing tedious handwork." (Son for his mother, age 92. Condition: essential tremor)

"I had shingles about 4 years ago and it was excruciating. Recently, I felt an outbreak coming on again in a 7-8" patch on my upper leg and wanted to head it off at the pass. I applied the oil blend all over the entire area as a test. In under 30 minutes, the pain (which was a 10) was only a 2. The spot vanished by the next day. I was shocked and amazed, and so far, no outbreak more than 6 months later." (54-year old male. Condition: Shingles)

The purpose of this invention, what is claimed and the methods for its use are as follows:

1. A composition of eight essential oils containing sesqiterpene compounds as active ingredients for therapeutic relief of neurological ailments, said composition comprising 2-18% oil from the grasses of *Vetiveria zizanioides,* 7-23% oil from the flowers of *Cananga odorata,* 7-23% oil from the wood of *Santalum spicatum* trees, 11-27% oil from the leaves of *Pogostemon cablin,* 5-31% oil from the wood of *Juniperus virginiana,* 7-23% oil from the resin of *Commiphora myrrha,* oil from the resin of *Boswellia carterii* trees, and 5-25% oil from the flowers of *Lavandula officinalis.*

2. A method of topical administration comprising applying the composition of claim 1 either alone, or with unscented lotion, face wash, body wash, shampoo, conditioner, or bath salts, to the skin or scalp of the subject in need thereof with deep massage for relief of neurological ailments.

3. An aromatherapy method comprising inhaling the composition of claim 1 through nasal passage of the subject in need thereof using an inhaler stick, paraffin wax candles, or sprays for relief of neurological ailments.

\* \* \* \* \*